US012605503B2

(12) United States Patent
Rasmussen

(10) Patent No.: US 12,605,503 B2
(45) Date of Patent: Apr. 21, 2026

(54) CANNULA SYSTEM WITH RIGID CANNULA

(71) Applicant: Roche Diabetes Care, Inc.,
Indianapolis, IN (US)

(72) Inventor: Mads Bjoern Rasmussen, Weinheim
(DE)

(73) Assignee: Roche Diabetes Care, Inc.,
Indianapolis, IN (US)

( * ) Notice: Subject to any disclaimer, the term of this
patent is extended or adjusted under 35
U.S.C. 154(b) by 851 days.

(21) Appl. No.: 17/752,291

(22) Filed: May 24, 2022

(65) Prior Publication Data

US 2022/0280716 A1     Sep. 8, 2022

Related U.S. Application Data

(63) Continuation of application No.
PCT/EP2020/083140, filed on Nov. 24, 2020.

(30) Foreign Application Priority Data

Nov. 26, 2019     (EP) ..................................... 19211423

(51) Int. Cl.
A61M 5/158          (2006.01)
A61M 5/32          (2006.01)
(52) U.S. Cl.
CPC ..... A61M 5/158 (2013.01); A61M 2005/1585
(2013.01); A61M 2005/3201 (2013.01)
(58) Field of Classification Search
CPC .......... A61M 5/158; A61M 2005/1585; A61M
2005/3201; A61M 5/14244
See application file for complete search history.

(56) References Cited

U.S. PATENT DOCUMENTS

| | | | |
|---|---|---|---|
| 2002/0161332 A1 | 10/2002 | Ramey | |
| 2002/0173769 A1 | 11/2002 | Gray et al. | |
| 2003/0220619 A1* | 11/2003 | Polidoro | ........... A61M 25/0637 |
| | | | 604/263 |

(Continued)

FOREIGN PATENT DOCUMENTS

| | | |
|---|---|---|
| JP | 2005-515798 A | 6/2005 |
| JP | 2007-511325 A | 5/2007 |

(Continued)

OTHER PUBLICATIONS

International Search Report and Written Opinion of the International Searching Authority, PCT/EP2020/083140, Jan. 26, 2021, 10 pages.

*Primary Examiner* — Theodore J Stigell
(74) *Attorney, Agent, or Firm* — Bose McKinney &
Evans LLP

(57)          ABSTRACT

Disclosed is a cannula system having a rigid cannula, a cannula assembly and an insertion assembly. The rigid cannula is connected to the cannula assembly. The cannula assembly has a septum mounted to a mounting structure of the cannula assembly, a connecting structure for reversibly or irreversibly connecting the cannula assembly to a cannula assembly holder, a cavity being at least partially formed by the septum. The rigid cannula is in fluidic communication with the cavity. Furthermore, the insertion assembly has a rigid needle at least partially penetrating the septum and an attachment structure for reversibly attaching the insertion assembly to the cannula assembly.

12 Claims, 1 Drawing Sheet

(56)                    References Cited

U.S. PATENT DOCUMENTS

| | | | |
|---|---|---|---|
| 2005/0107743 A1* | 5/2005 | Fangrow ............... | A61M 5/158 |
| | | | 604/164.01 |
| 2005/0245874 A1 | 11/2005 | Carrez et al. | |
| 2007/0185455 A1* | 8/2007 | Fangrow ............... | A61M 25/02 |
| | | | 604/288.02 |
| 2014/0088550 A1 | 3/2014 | Benéet al. | |
| 2014/0276576 A1 | 9/2014 | Cole et al. | |

FOREIGN PATENT DOCUMENTS

| | | | |
|---|---|---|---|
| WO | WO 02/094352 A2 | 11/2002 | |
| WO | WO 2005/049117 A2 | 6/2005 | |
| WO | WO 2009/046989 A2 | 4/2009 | |
| WO | WO 2018/100072 A1 | 6/2018 | |

* cited by examiner

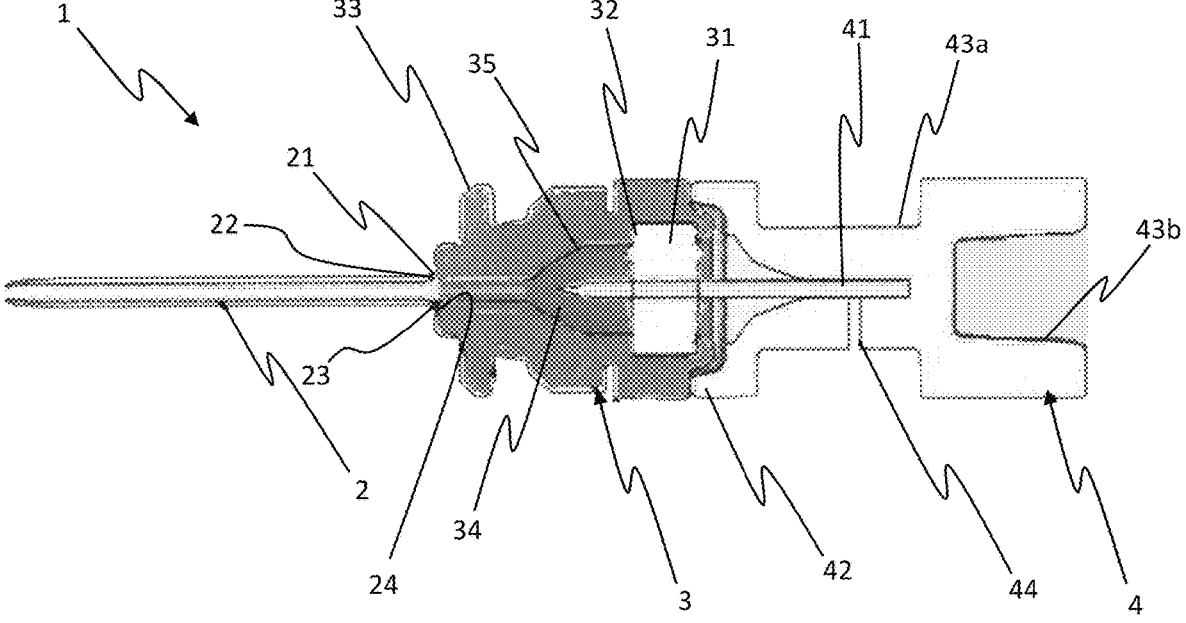

CANNULA SYSTEM WITH RIGID CANNULA

RELATED APPLICATIONS

This application is a continuation of PCT/EP2020/ 083140, filed Nov. 24, 2020, which claims priority to EP 19 211 423.9, filed Nov. 26, 2019, both of which are hereby incorporated herein by reference.

BACKGROUND

This disclosure lies in the field of infusion technology. More particularly, it is related to a cannula system comprising a rigid cannula and the use of such a cannula system in an infusion system.

Infusion pumps are used for parenterally providing patients with liquid medicaments over longer time periods. Nowadays, infusion pumps with very small dimensions are available that can be carried by the patient on the body. Such small-sized ambulatory infusion pumps are particularly useful for metering small doses of highly effective liquid medicaments, such as insulin for the treatment of diabetes, or analgesics for pain therapy, which are conveyed through a cannula into the tissue of a patient.

In one approach, an infusion pump, carried somewhere on the body, e.g., attached to a belt, is fluidly connected via flexible tubing to an infusion site interface, also called insertion head, that is attached to the body of the patient. The infusion site interface comprises a cannula system with a cannula to be inserted into the body tissue, a housing and connector means for fluidly connecting the cannula with the flexible tubing connected to the upstream infusion pump. The infusion site interface may be attached to the patient via an infusion pump cradle. The tubing can be repeatedly connected and disconnected from the infusion site interface. The connector means may for example comprises a septum sealingly closing the fluid system of cannula and housing. The septum can be penetrated by a hollow needle, for reversibly establishing a fluid connection. The cannula may be made of a flexible material and thus be a soft cannula. Such cannulas are more comfortable for their users, particularly during body movements. Since flexible cannulas cannot be inserted directly into the tissue, an additional piercing device, e.g., in the form of a rigid piercing needle made from metal, is arranged inside the flexible cannula. A pointed end of the piercing device protrudes from the proximal end of the cannula, the cannula that will be open toward the interstitial fluid. After inserting the piercing device and the stabilized cannula into the body tissue, the rigid piercing device is removed from the flexible cannula. The cannula remains in the body tissue. Generally, a piercing needle is arranged in such a way that it penetrates the septum, which after withdrawal of the piercing needle sealingly closes the distal end of the now open cannula fluid path.

In another approach, the infusion pump device is directly fluidly connected with the infusion site interface. The fluid connection between pump and cannula is established by a hollow connector needle of the pump, reversibly penetrating a septum of the cannula unit that sealingly closes the distal end of the cannula fluid path. Advantageously, the pump can be repeatedly connected and disconnected from the infusion site interface.

While the use of soft or flexible cannulas is in general preferred due to the increased wearing comfort for the user, these can also be problematic for certain patients suffering from intolerances against the soft cannula material, for example latex, silicone or rubber, leading to skin irritation and/or infections. For such patients, metallic cannulas, for example, steel cannulas, provide a favorable alternative. The overall setup for rigid cannulas is typically less complicated, as the piercing needle is typically dispensed with.

SUMMARY

This disclosure advances the state of the art regarding cannula systems with a rigid cannula as used in the context of liquid drug infusion, thereby avoiding disadvantages of the prior art fully or partly.

In advantageous embodiments, a cannula system with increased compatibility for the patient, in particular for a patient with an intolerance against silicone, rubber or the like is provided.

In further advantageous embodiments, a cannula system is provided in which the locking of the rigid cannula is improved and/or the occurrence of leakage is diminished.

According to an aspect of this disclosure, disclosed is a cannula system comprising a rigid cannula, a cannula unit (also referred to herein as a "cannula assembly") to which the rigid cannula is connected, preferably directly connected, and an insertion unit (also referred to herein as an "insertion assembly"). The cannula unit comprises a septum, which is mounted to a mounting structure of the cannula unit. The mounting structure may for example be a groove or recess formed by inner walls of the cannula unit. For example, the septum may be crimped or clamped to the mounting structure, thereby establishing a tight sealing between the septum and the inner walls of the cannula unit. The cannula unit further comprises a connecting structure (also referred to herein as a "connector") for reversibly or irreversibly connecting the cannula unit to a cannula unit holder. The cannula unit holder may typically be an infusion pump cradle for attaching the cannula unit to the patient's body. Additionally, the cannula unit comprises a cavity for receiving the liquid medicament when the cannula unit is connected to an infusion pump by piercing the septum with an infusion pump cannula. The cavity is at least partially formed by the septum. The rigid cannula is in fluidic communication with the cavity. In order to establish a releasable but also stable connection between the cannula unit and the insertion unit, the insertion unit contains a rigid needle, which at least partially penetrates the septum of the cannula unit. Thus, the rigid needle prevents essentially any lateral movement of the insertion unit with respect to the cannula unit, with the exception of any movement enabled by the elastic nature of the septum. The rigid needle preferably extends up to the cavity. The rigid needle preferably does not extend into rigid cannula, preferably the tip of the rigid needle does not extend into the lumen of the rigid cannula. Due to its rigidness, the rigid cannula is able to penetrate and insert into the skin without help of an enveloping or enveloped rigid insertion needle. This is contrary to soft cannulas which require a rigid insertion needle that either envelops the soft cannula or is enveloped by the soft cannula for stabilization of the soft cannula at least during insertion of the soft cannula into the skin. This difference is associated with the advantage that it simplifies the design of the cannula system and the rigid cannula insertion process when compared to systems using a soft cannula and a rigid insertion needle. For example with the prior arts' soft cannula and rigid insertion needle combinations it is necessary to insert and withdraw the rigid insertion needle while leaving the inserted soft cannula in place. Such devices are complex since the insertion needle and the soft cannula are in direct mechanical contact with each other during insertion into the skin whereas in the case of this disclosure there is no need for such a complex insertion needle withdrawal process since the rigid insertion needle is not in direct mechanical contact with the rigid cannula. The insertion unit further comprises an attachment structure configured to reversibly attaching the insertion unit to the cannula unit.

As used herein, the term "septum" is readily understood by those skilled in the art and is typically an engineered element, for example in the form of a membrane or plug, for sealingly separating a first side and second side in a fluid, i.e., gas and/or liquid, tight seal, which can be pierced by a needle or a cannula. Typically, a septum does not comprise an opening or a puncture, which passes through the septum from the first side to the second side, before a needle or a cannula has been pierced through the septum. Thus, the septum may be referred to as a puncture-less septum. Consequently, a stump needle cannot be easily pierced through the septum without exerting high forces. Apart from the first surface being shaped as explained above and further below, the first and second surface may preferably be coplanar.

The rigid cannula may be made from any suitable metal, preferably steel, particularly stainless steel. Additionally, at least the cannula unit may be injection molded, preferably directly injection molded onto the rigid cannula. It is understood that the rigid needle is typically a solid body, i.e., the rigid needle may not comprise a through hole or an orifice and may therefore not be a cannula.

In some embodiments, the rigid needle penetrates the septum in an essentially central position of the septum, when the insertion unit is attached to the cannula unit. A septum having two coplanar surfaces is thus penetrated essentially along a central axis being perpendicular to both coplanar surfaces. Such an arrangement facilitates establishing the connection between the cannula unit and the insertion unit.

In further embodiments the cavity is formed by inner walls of the cannula unit and the septum.

In some embodiments, the rigid cannula comprises a locking structure (also referred to herein as a lock") for fixedly connecting the cannula to the cannula unit.

In certain embodiments the locking structure provides a positive lock and/or an adhesive bond between the rigid cannula and the cannula unit. For example, an adhesive such as a glue may be used to lock the cannula to the cannula unit.

In some embodiments the locking structure includes at least one protrusion 22, preferably a collar 23 which is preferably arranged at the most distal end of the rigid cannula. It is understood that the distal part of the cannula refers to the end area of the cannula that is facing away from the patient in an operative state. Alternatively, or additionally, the locking structure may comprise at least one hole 24, preferably a through bore or a blind hole. Such locking structures are preferred, in particular if the cannula unit is injection molded. During production, the material can enter the hole or surround the protrusion, which provides a strong positive locking connection after cooling.

In further embodiments the insertion unit comprises connecting means for connecting the insertion unit to an inserter. The connecting means may comprise any suitable connecting mechanism, such as bayonet, snap fit, latches, hooks and the like. Typically, the connecting means are configured for providing a releasable connection between the insertion unit and the inserter.

In some embodiments the insertion unit comprises a slit extending towards the rigid needle. The slit may comprise an adhesive such as a glue. The slit may for example be arranged transversal to the rigid needle. The slit enables a secure connection of the needle within the insertion unit and further simplify the production process of the insertion unit.

In further embodiments the rigid needle is unmovably connected to the rest of the insertion unit.

In some embodiments the attachment structure comprises a releasable adhesive or a releasable positive locking structure. The releasable adhesive may for example be an adhesive layer, whose connecting force may readily be overcome by a user. The positive locking structure may comprise any suitable form-lock mechanism, such as bayonet, snap fit, latches, hooks and the like.

In further embodiments a force required for releasing the cannula unit from the insertion unit is smaller than a force exerted by the connecting structure for reversibly or irreversibly connecting the cannula unit to the cannula unit holder and/or smaller than a force required to separate the rigid cannula from the cannula unit. Thus, if a pulling force is exerted on the insertion unit away from the cannula unit, the attachment structure is released and the insertion unit is separated from the cannula unit, while the rigid cannula remains connected to the cannula unit and the cannula unit remains connected to a cannula unit holder.

According to a further aspect of this disclosure, the overall objective is achieved by an infusion system comprising a cannula system according to any of the embodiments as described herein.

According to a further aspect of this disclosure, the overall objective is achieved by the use of a cannula system according to any of the embodiments as described herein in an infusion system.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein:

FIG. 1 shows a schematic cross-sectional view of a cannula system according to an embodiment of this disclosure.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

FIG. 1 depicts a cannula system 1 with rigid steel cannula 2, cannula unit 3 (also referred to herein as a "cannula assembly") and insertion unit 4. Rigid cannula 2 is connected to cannula unit 3 via locking structure 21 (also referred to herein as a "lock"), which in the particular embodiment shown, comprises an enlarged cross-section at the most distal end area of cannula 2, such as a collar 23. Cannula unit 3 comprises septum 31, which is mounted to mounting structure 32 of cannula unit 3. As can be seen, mounting structure 32 is formed by inner wall 35 of the cannula unit 3, which crimp the septum into cannula unit 3. Cannula unit 3 further comprises cavity 34, which is partially formed by septum 31 and partially by inner wall 35 of cannula unit 3. As can be readily seen from FIG. 1, rigid cannula 2 is in fluidic communication with cavity 34, such that a liquid medicament can be delivered to cavity 34 and infused into the patient via cannula 2 in an operative state, i.e., in a state in which inserter 4 is removed and an infusion pump is in fluidic communication with cavity 34 via septum 31. Cannula unit 3 further comprises connecting structure 33 for connecting cannula unit 3 to an infusion pump cradle. As shown, connecting structure 33 comprises protrusions and recesses which may be part of a snap fit connection.

Insertion unit 4 comprises rigid needle 41, which maintains insertion unit 4 and cannula unit 3 axially aligned to each other. Rigid needle 41 penetrates septum 31 in an essentially central position and preferably extends up to the cavity 34. Rigid needle 41 preferably does not extend into rigid cannula 2, in particular, the tip of the rigid needle 41 does not extend into the lumen of the rigid cannula 2. Due to its rigidness, the rigid cannula 2 is able to penetrate and insert into the skin without help of a rigid insertion needle that envelopes or is enveloped by the rigid cannula 2. This is in contrast to hitherto known soft cannulas which require a rigid insertion needle that either envelops the soft cannula or is enveloped by the soft cannula for stabilization of the soft cannula at least during insertion of the soft cannula into the skin. Insertion needle 41 may be fixedly connected to the insertion unit by an adhesive, which is provided within slit 44. As can be seen, slit 44 extends transversally towards needle 41, such that the adhesive can fixedly connect insertion needle 41 and insertion unit 4. It should be noted that in contrast to rigid cannula 2, needle 41 aims to provide a fixed connection, thus needle 41 is typically a compact body, i.e., is not a hollow needle. Insertion unit 4 further comprises attachment structure 42 for releasably connecting insertion unit 4 and cannula unit 3. Via connecting means 43a and 43b, the insertion unit 4, respectively the cannula system 1 may be connected to an inserter as known in the prior art. In use, cannula system 1 is connected to an inserter, inserted into the patient, upon which cannula unit 1 is preferably connected to an infusion pump cradle via connecting structure 33 and then the insertion unit is released. Importantly, attachment structure 42 is in general configured such that a force required for releasing the cannula unit 3 from the insertion unit 4 is smaller than a force exerted by the connecting structure 33 for reversibly or irreversibly connecting the cannula unit 3 to the cannula unit holder (cannula holder not shown) and/or smaller than a force required to separate rigid cannula 2 from cannula unit 3.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A cannula system, comprising:
   a cannula assembly comprising a septum mounted to a mounting structure of the cannula assembly, a connector configured for reversibly or irreversibly connecting the cannula assembly to a cannula assembly holder, and a cavity at least partially formed by the septum;

a rigid cannula connected to the cannula assembly and having a lumen in fluidic communication with the cavity;

an insertion assembly having a rigid needle;

an attachment structure configured for reversibly attaching the insertion assembly to the cannula assembly, wherein the rigid needle penetrates the septum without extending into the lumen of the rigid cannula and has a tip disposed within the cavity when the insertion assembly is attached to the cannula assembly; and wherein the rigid cannula includes a protrusion protruding from the cannula in the form of a collar and the rigid cannula is fixedly connected to the cannula assembly by a lock which comprises at least one hole comprising a through bore or a blind hole in the collar wherein material forming the mounting structure is disposed within the at least one hole and surrounds the protrusion.

2. The cannula system according to claim 1, wherein the rigid needle penetrates the septum in an essentially central position of the septum, when the insertion assembly is attached to the cannula assembly.

3. The cannula system according to claim 1, wherein the cavity is formed by inner walls of the cannula assembly and the septum.

4. The cannula system according to claim 1, wherein the lock is arranged at the most distal part of the rigid cannula.

5. The cannula system according to claim 1, wherein the insertion assembly comprises a second connector configured for connecting the insertion assembly to an inserter.

6. The cannula system according to claim 1, wherein the insertion assembly comprises a slit extending towards the rigid needle, wherein the slit comprises an adhesive.

7. The cannula system according to claim 1, wherein the rigid needle is unmovably connected to the rest of the insertion assembly.

8. The cannula system according to claim 1, wherein the attachment structure comprises a releasable form locking structure.

9. The cannula system according to claim 8, wherein a force required for release of the cannula assembly from the insertion assembly is smaller than a force exerted by the connector for reversibly or irreversibly connecting the cannula assembly to the cannula assembly holder and smaller than a force required to separate the rigid cannula from the cannula assembly.

10. The cannula system according to claim 1, wherein a force required for release of the cannula assembly from the insertion assembly is smaller than a force exerted by the connector for reversibly or irreversibly connecting the cannula assembly to the cannula assembly holder and smaller than a force required to separate the rigid cannula from the cannula assembly.

11. The cannula system according to claim 10, wherein the attachment structure reversibly attaching the insertion assembly to the cannula assembly comprises a releasable adhesive.

12. A method of using a cannula system comprising:
    providing a cannula system according to claim 1; and
    administering a drug to a patient with the cannula system.

* * * * *